US006080584A

United States Patent [19]
Alfano et al.

[11] Patent Number: 6,080,584
[45] Date of Patent: Jun. 27, 2000

[54] METHOD AND APPARATUS FOR DETECTING THE PRESENCE OF CANCEROUS AND PRECANCEROUS CELLS IN A SMEAR USING NATIVE FLUORESCENCE SPECTROSCOPY

[75] Inventors: Robert R. Alfano, Bronx, N.Y.; Singaravelu Ganesan, Edison; Yury Budansky, Oakland, both of N.J.

[73] Assignee: The Research Foundation of City College of New York, New York, N.Y.

[21] Appl. No.: 08/982,947

[22] Filed: Dec. 2, 1997

Related U.S. Application Data

[60] Provisional application No. 60/032,078, Dec. 2, 1996.

[51] Int. Cl.⁷ .................................................. G01N 21/64
[52] U.S. Cl. ............................ 436/63; 436/64; 436/172; 422/82.08
[58] Field of Search .............................. 436/63, 64, 172; 422/82.08; 250/459.1, 461.2

[56] References Cited

U.S. PATENT DOCUMENTS

| | | | |
|---|---|---|---|
| 4,755,684 | 7/1988 | Leiner et al. | 250/461.1 |
| 4,930,516 | 6/1990 | Alfano et al. | 128/665 |
| 5,042,494 | 8/1991 | Alfano | 128/665 |
| 5,061,075 | 10/1991 | Alfano et al. | 356/417 |
| 5,131,398 | 7/1992 | Alfano et al. | 128/665 |
| 5,348,018 | 9/1994 | Alfano et al. | 128/665 |
| 5,413,108 | 5/1995 | Alfano | 128/665 |
| 5,450,857 | 9/1995 | Garfield et al. | 128/778 |
| 5,474,910 | 12/1995 | Alfano | 435/34 |
| 5,612,540 | 3/1997 | Richards-Kortum et al. | 250/461.2 |
| 5,635,402 | 6/1997 | Alfano et al. | 436/63 |

OTHER PUBLICATIONS

Lohmann, W. et al, "Autofluorescence of tissue surrounding malignant tumors" Proc. SPIE–Int. Soc. Opt. Eng. (1998) vol. 3251 (Coherence Domain Optical Methods in Biomedical Science and Clinical Applications II) pp. 165–171.

Primary Examiner—Jeffrey Snay
Attorney, Agent, or Firm—Kriesman & Kriesman

[57] ABSTRACT

A method and apparatus for examining a cell smear for the purpose of detecting the presence of cancerous and precancerous cells located therein. In a preferred embodiment, the method comprises illuminating at least a portion of the cell smear with light of a first wavelength, whereby native fluorescence is emitted therefrom. Next, the intensity of native fluorescence emitted from the illuminated area is measured at a second wavelength and at a third wavelength as a function of location within the illuminated area. The first, second and third wavelengths are chosen so that the ratio of fluorescence intensities at the second and third wavelengths is indicative of a carcinomatous condition. Next, the ratio of intensities measured at the second and third wavelengths is determined to obtain a value for each location within the illuminated area. Finally, a map is generated of all the cells present within the illuminated area using the calculated values. The map not only shows the spatial distribution of cells located within the area but also indicates by color coding or shading the carcinomatous condition of each cell therein.

11 Claims, 12 Drawing Sheets

Averaged excitation spectrum and difference spectra of normal and malignant cells from six individual experiments for 340 nm emission Averaged fluorescence emission spectra of normal and malignant cells for excitation at 275 nm from six individual experiments.

Averaged fluorescence emission spectra of normal and malignant cells for excitation at 285 nm from six individual experiments.

Averaged fluorescence emission spectra of normal and malignant cells for excitation at 310 nm from six individual experiments.

Averaged fluorescence emission spectra of normal and cancer breast smear at 280 nm excitation.

Averaged excitation spectra and difference spectrum of normal and cancer breast smear for 340 nm emission.

Averaged diffuse reflectance spectra of normal and cancer breast smear.

Standard method to take sample.

Making smear on slide.

Stored slide with smear for fluorescence measurement.

Glass rod

Smear on rod ready for measurement

Stored rod for fluorescence measurement

METHOD AND APPARATUS FOR DETECTING THE PRESENCE OF CANCEROUS AND PRECANCEROUS CELLS IN A SMEAR USING NATIVE FLUORESCENCE SPECTROSCOPY

CROSS-REFERENCE TO RELATED APPLICATIONS

The present application claims the benefit under 35 U.S.C. 119(e) of U.S. Provisional Patent Application Ser. No. 60/032,078, filed Dec. 2, 1996, the disclosure of which is incorporated herein by reference.

BACKGROUND OF THE INVENTION

The present invention relates generally to the detection of cancer and precancerous conditions and more particularly to the detection of cancerous and precancerous cells in cell smears.

Because a sufficiently effective method has not yet been developed to prevent cancer, cancer research has focused on the most effective ways to treat cancer. As different as the various forms of treatment have been—ranging from excision to radiation to chemotherapy—all treatments have relied upon one crucial step, the detection of cancer. The importance of detection cannot be stressed enough. Early detection not only indicates the presence of cancer (or of a precancerous condition) but also may give an indication as to where the cancer originated and what type of treatment will be the most safe and effective. In addition to being used to detect cancer early, detection methods may also be used to determine whether treatment methods have been successful in eradicating cancer from a patient.

At present, methods for detecting most forms of cancer have relied primarily on the use of X-rays, nuclear magnetic resonance, nuclear radiation or invasive methods based on chemical laboratory analysis and biopsy. To detect cervical cancer, one commonly employs the Pap smear technique. Pap smears are typically performed by obtaining a sample of cells from a patient and smearing them on a slide. Typically, the cells are stained to make them more visible under microscopic examination. The smeared slide is then examined under a microscope, typically by a physician or trained technician. The physician or technician detects cancerous or precancerous cells in the smear based on certain criteria, such as cell morphology. As can readily be appreciated, this means of detection is not exact and often results in errant results. Moreover, this technique is cumbersome and time consuming and is not in situ or in real time.

Recently, optical spectroscopy has been investigated as a means of detecting cancer. For example, in U.S. Pat. No. 5,042,494, inventor Alfano, which issued Aug. 27, 1991, and which is incorporated herein by reference, there is disclosed a method and apparatus for detecting the presence of cancerous tissue using native visible luminescence. The tissue to be examined is excited with a beam of light that causes the tissue to fluoresce over a spectrum of wavelengths. The intensity at which the the excited tissue fluoresces can be measured either over a spectrum or at a predetermined number of preselected wavelengths. By determining the wavelength(s) at which maximum intensity(ies) are attained for the tissue in question and by comparing these peak wavelengths, either visually or electronically, to the peak wavelength(s) derived from a known non-cancerous tissue, or by comparing the luminescence spectrum of the excited tissue with the luminescence spectrum of a known non-cancerous tissue and/or known cancerous tissue or the excitation spectra of the excited tissue with the excitation spectra of known cancerous and/or known non-cancerous tissue, one can determine the carcinomatoid status of the tissue in question.

In U.S. Pat. No. 5,131,398, inventors Alfano et al., which issued Jul. 21, 1992, and which is incorporated herein by reference, there is disclosed a method and apparatus for distinguishing cancerous tumors and tissue from benign tumors and tissue or normal tissue using native fluorescence. The tissue to be examined is excited with a beam of monochromatic light at 300 nm. The intensity of the native fluorescence emitted from the tissue is measured at 340 nm and at 440 nm. The ratio of the two intensities is then calculated and used as a basis for determining if the tissue is cancerous as opposed to benign or normal.

In U.S. Pat. No. 5,413,108, inventor Alfano, which issued May 9, 1995, and which is incorporated herein by reference, there is disclosed a method and apparatus for examining a two-dimensional region of a tissue sample. This is accomplished, according to one embodiment, by illuminating, i.e., exciting, the two-dimensional tissue sample with light at a first wavelength. The resultant fluorescence is then measured at an emission wavelength as a function of location within the two-dimensional tissue sample. The two-dimensional tissue sample is then illuminated again with light at a second wavelength, and the resultant fluorescence is measured at the same emission wavelength. The two excitation wavelengths and the emission wavelength are appropriately chosen so that the ratio or difference of fluorescence intensities at the emission wavelength is indicative of the carcinomatoid condition of the tissue. A value, such as a ratio or difference, of the respective intensity measurements obtained at each location of the tissue sample is then calculated. These values are then compared to appropriate standards, and the results are depicted in the form of a map. The invention is premised on the discovery that certain native, commonly-occurring molecules, such as collagen, NAD+/NADH, NADP+/NADPH, flavins, tryptophan and elastin fluoresce differently in cancerous tissue than in non-cancerous tissue.

It should be noted that, in the three patents discussed above, the sample examined is a tissue, not a cell smear.

In U.S. Pat. No. 5,635,402, inventors Alfano et al., which issued Jun. 3, 1997, and which is incorporated herein by reference, there is disclosed a technique for determining whether a cell is malignant as opposed to non-malignant using extrinsic fluorescence spectroscopy. The technique is premised on the principle that certain fluorescent dyes preferentially stain malignant cells as opposed to non-malignant cells. Accordingly, by exposing a cell to the fluorescent dye, irradiating the cell with light of such a wavelength as to cause the dye to fluoresce, measuring the intensity of fluorescence at a wavelength indicative of fluorescence of the dye, and comparing the fluorescence intensity to standards obtained from malignant cells and nonmalignant cells, it is possible for one to accurately classify the cell as being either malignant or non-malignant. The present invention also relates to an automated system which applies the principles of the aforementioned technique to depict the spatial distribution of cells within an area of a Pap smear-type sample and to characterize each of the cells as being malignant or nonmalignant.

It is to be noted that, in the case of the aforementioned patent, extrinsic fluorescence spectroscopy, as opposed to native fluorescence spectroscopy, is used.

SUMMARY OF THE INVENTION

It is an object of the present invention to provide a novel technique for detecting cancer and precancerous conditions.

It is another object of the present invention to provide a novel technique as described above that employs native fluorescence spectroscopy. For purposes of the present specification and claims, the term "native fluorescence spectroscopy" is intended to include both native fluorescence excitation spectroscopy and native fluorescence emission spectroscopy.

According to one aspect of the invention, there is described a method of detecting cancer or a precancerous condition in a patient comprising the steps of (a) obtaining a sample of cells from the patient; (b) preparing a cell smear with said sample of cells; and (c) using native fluorescence spectroscopy to detect the presence of cancerous or precancerous cells in said cell smear.

In one embodiment of the aforementioned method, said native fluorescence spectroscopy using step comprises (i) illuminating at least a portion of the cell smear with light of a first wavelength, whereby native fluorescence is emitted therefrom, (ii) measuring the intensity of native fluorescence emitted from the illuminated area at a second wavelength and at a third wavelength as a function of location within the illuminated area, said first, second and third wavelengths being such that the ratio or difference of fluorescence intensities at said second and third wavelengths is indicative of a carcinomatous condition, (iii) determining the ratio or difference of intensities measured at said second and third wavelengths to obtain a value for each location within the illuminated area; and (iv) generating a map of cells present within the illuminated area wherein said map indicates the carcinomatous condition of each cell therein.

The cell smear of the present invention is not limited to cells derived from the cervix and can be used for cells obtained from a number of tissues and/or organs including the colon, the rectum, the lungs, the aerodigestive tract and the like.

The present invention is also directed to an automated system for examining a cell smear for the presence of cancerous or precancerous cells therein.

Additional objects, features, aspects and advantages of the present invention will be set forth, in part, in the description which follows and, in part, will be obvious from the description or may be learned by practice of the invention. In the description, reference is made to the accompanying drawings which form a part thereof and in which is shown by way of illustration specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate preferred embodiments of the invention and, together with the description, serve to explain the principles of the invention. In the drawings wherein like reference numerals represent like parts.

DETAILED DESCRIPTION OF PREFERRED EMBODIMENTS

Figure 1:
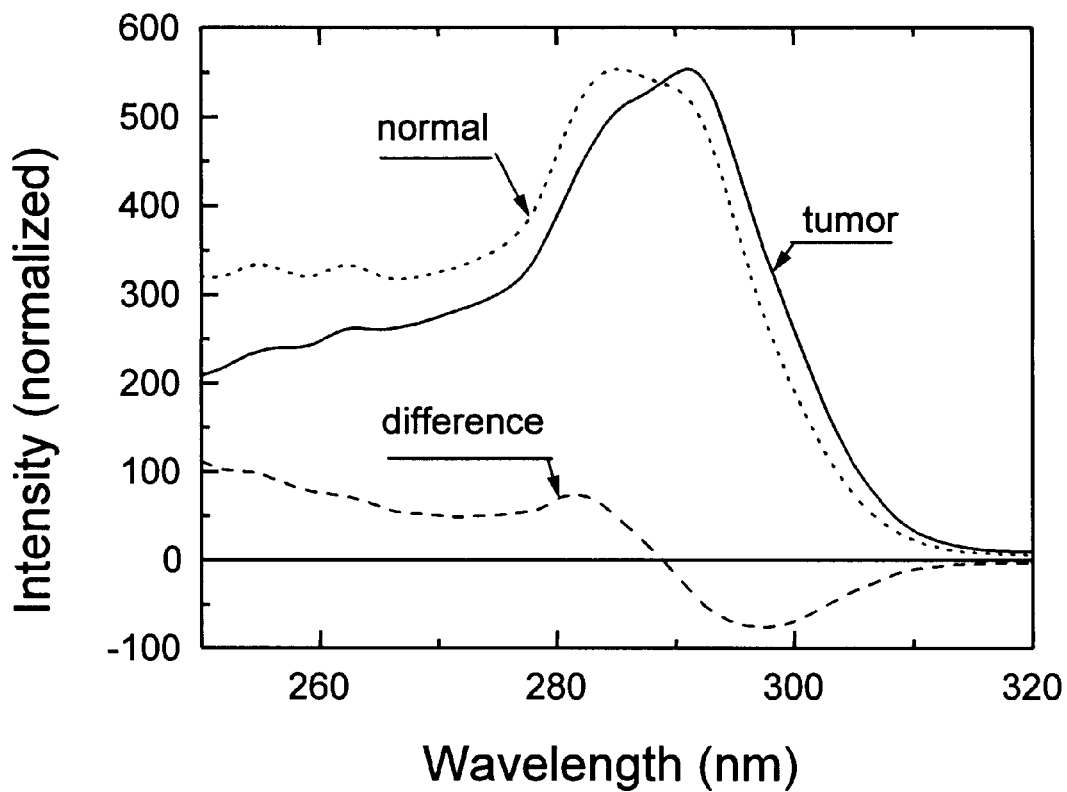
FIG. 1 is a graphic representation of the averaged excitation spectra for normal and malignant human epithelial cells excited over the 250 nm to 320 nm spectral region, with an emission wavelength of 340 nm.

As a technical underpinning for the present invention, the present inventors conducted certain studies on the native fluorescence of both normal and malignant human epithelial cells. Referring now to FIG. 1, there are shown the averaged excitation spectra for normal and malignant human epithelial cells excited over the 250 nm to 320 nm spectral region, with an emission wavelength of 340 nm. The average spectra were obtained by normalizing the peak of each curve to unity and averaging. From these spectra, it is apparent that there is a spectral difference between malignant and benign cells. More particularly, the following salient features between the normal and malignant curves are noted: (1) Two intensity peaks near 283 nm and 292 nm are observed for normal and malignant epithelial cells, respectively. (2) A normalized isosbestic point is observed at 289±2 nm for the cells. At this isosbestic point, the averaged excitation spectra of malignant and normal cells do not differ. (3) The intensity for normal cells in the 250–289 nm spectral region is higher than that for the malignant cells; consequently, the difference spectra is negative over this region. By contrast, the intensity for malignant cells in the 289–297 nm spectral region is higher than that for the normal cells; consequently, the difference spectrum is positive over this region. (4) The spectrum for the malignant cells is red-shifted as compared to that for the normal cells.

In an effort to quantify the above-discussed differences and to determine whether any diagnostic potential exists, two ratio parameters were introduced: $R_{e1} \equiv I_{289}/I_{250}$ and $R_{e2} \equiv I_{289}/I_{297}$ wherein $I_{297}$ and $I_{250}$ are the relative intensities of peak positions of the difference spectrum, and $I_{289}$ is the relative intensity at the "normalized isosbestic" point. The value of $R_{e1}$ is 2.86±0.52 for the malignant cells and 1.66±0.06 for the normal cells. This is due to the fact that the relative absorption at 250 nm, as compared to 289 nm, is lower for malignant cells than for normal cells. Similarly, the value of $R_{e2}$ is 1.36±0.14 for malignant cells and 1.86±0.05 for normal cells. This is because the relative absorption around 297 nm, as compared to 289 nm, is higher for malignant cells than for normal cells. Using t test, statistical significance was observed for $R_{e1}$ and $R_{e2}$ values between normal and malignant cells. The p value for both ratios was found to be p≡0.000, indicating a very high significance. These results were obtained by averaging six individual curves for malignant (squamous cell carcinoma) and the normal cells of head and neck.

Figure 2A:
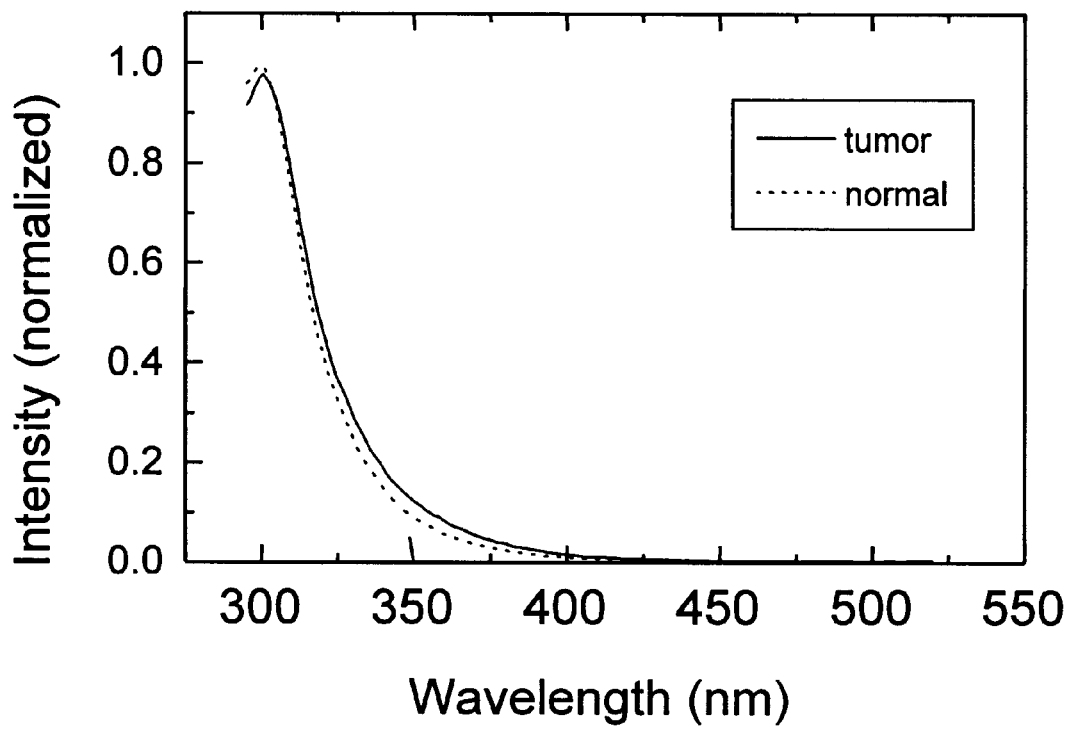
FIGS. 2(a) through 2(c) are graphic representations of emission spectra obtained at excitation wavelengths of 275 nm, 285 nm and 310 nm, respectively, for normal and malignant cells.
Figure 2B:
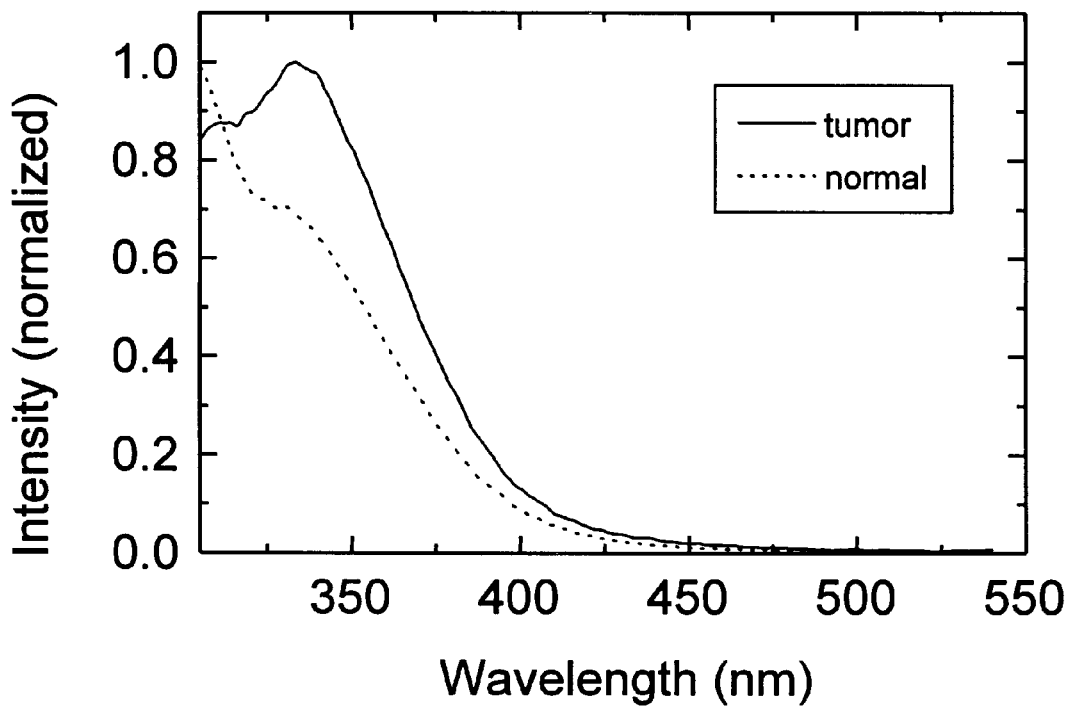
Figure 2C:
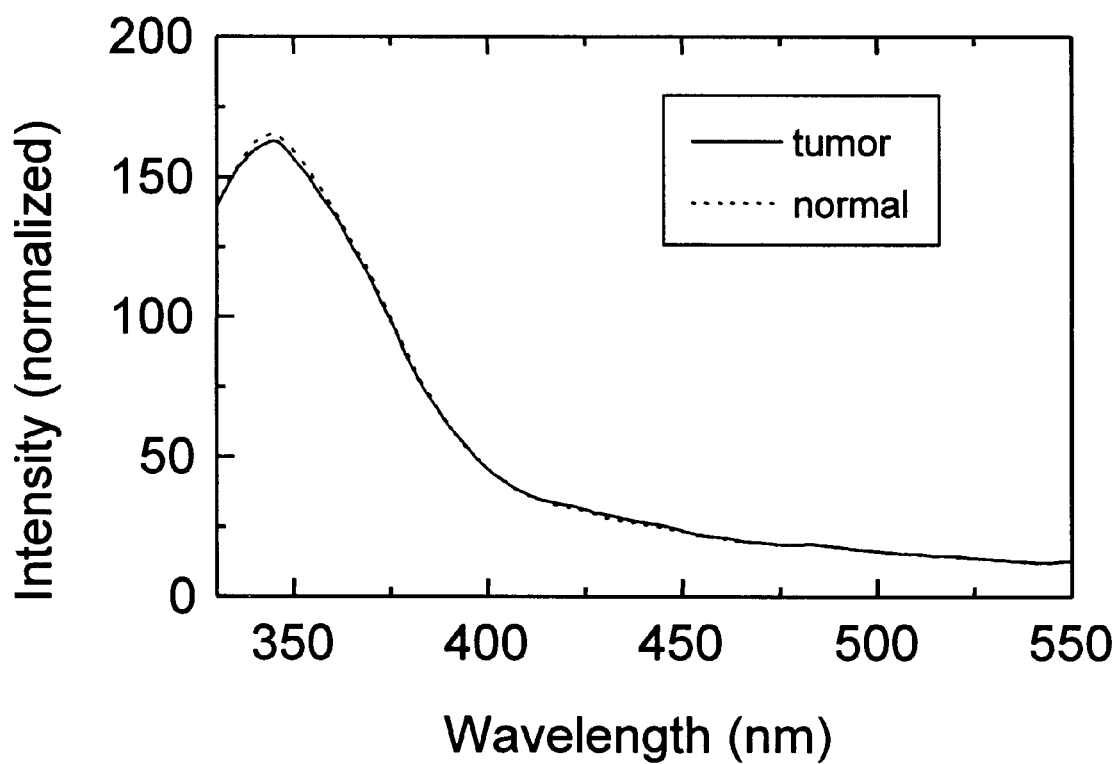

Although emission spectra were obtained for excitation wavelengths every 5 nm over the spectral region 250–310, FIGS. 2(a) through 2(c) show emission spectra obtained at excitation wavelengths of 275 nm, 285 nm and 310 nm, respectively, for normal and malignant cells. As can be seen in FIGS. 2(a) through 2(c), the wavelength of maximum emission differed depending on the excitation wavelength. (This phenomenon is not experienced when dealing with tissues, as opposed to cells. In fact, the maximum peak emission for tissues is around 340 nm (attributed to Trp), irrespective of the excitation wavelength over the 250–310 nm spectral region.) More particularly, the emission spectra for 275 nm excitation had a peak around 299 nm for both normal and malignant cells. The emission spectra for 285 nm excitation had two peaks around 310 nm and 335 nm for malignant cells and two peaks around 305 and 330 nm for normal cells. The averaged spectra for malignant cells experienced a small red shift as compared to the normal cells. This may be due to the presence of both Tyr and Trp at this excitation. For excitation at 310 nm, the averaged emission spectra for both the normal and malignant cells have similar spectral characteristics and no difference was observed at both 340 nm and 440 nm emission. The lack of a difference at 340 and 440 nm emission for 310 nm excitation result is most likely due to the absence of collagen and elastic in cells.

Figure 3:
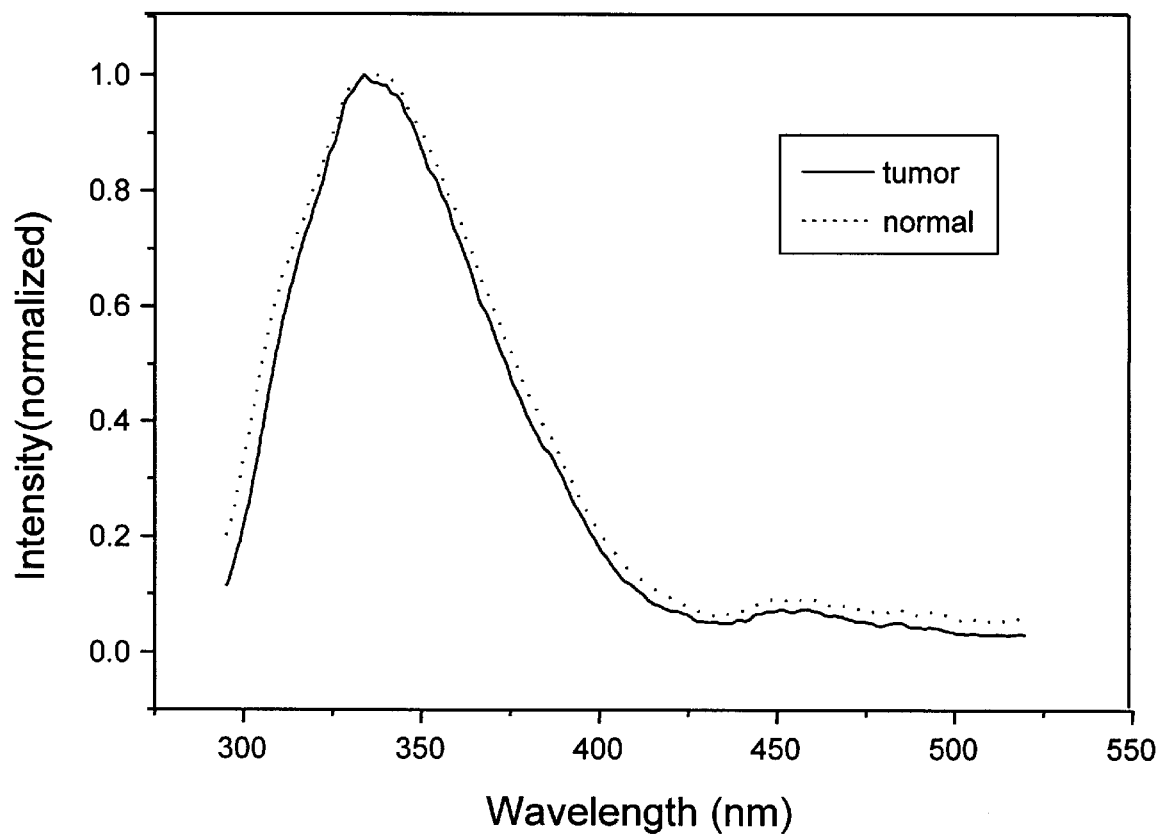
FIG. 3 is a graphic representation of the fluorescence spectra from 300 nm to 550 nm for normal and cancerous breast smears excited at 280 nm.

Referring now to FIG. 3, there are shown the fluorescence spectra from 300 nm to 550 nm for normal and cancerous breast smears excited at 280 nm. The smears were obtained by rubbing the normal and cancerous breast tissue samples onto quartz glass slides. As can be seen, the spectra for the normal and cancerous breast smears (which were normalized at a particular wavelength) were significantly different. Using these spectra, one can determine the status of an unknown smear by (1) taking the ratio of at least two or more emission wavelengths and comparing that to a comparable ratio obtained from known smears or (2) comparing the spectrum to the spectra from known smears. From FIG. 3, it can be seen that the ratio of fluorescence intensity at 340 and 440 nm differs greatly between cancerous (ratio value 18.0) and normal (ratio value 6.8) breast smears photoexcited at 280 nm. In general, the ratio for cancerous breast smears is greater than 7 whereas the ratio for normal breast smears is less than 7. Excitation wavelengths other than 280 nm may be necessary to differentiate normal and cancerous smears of a different origin.

Figure 4:
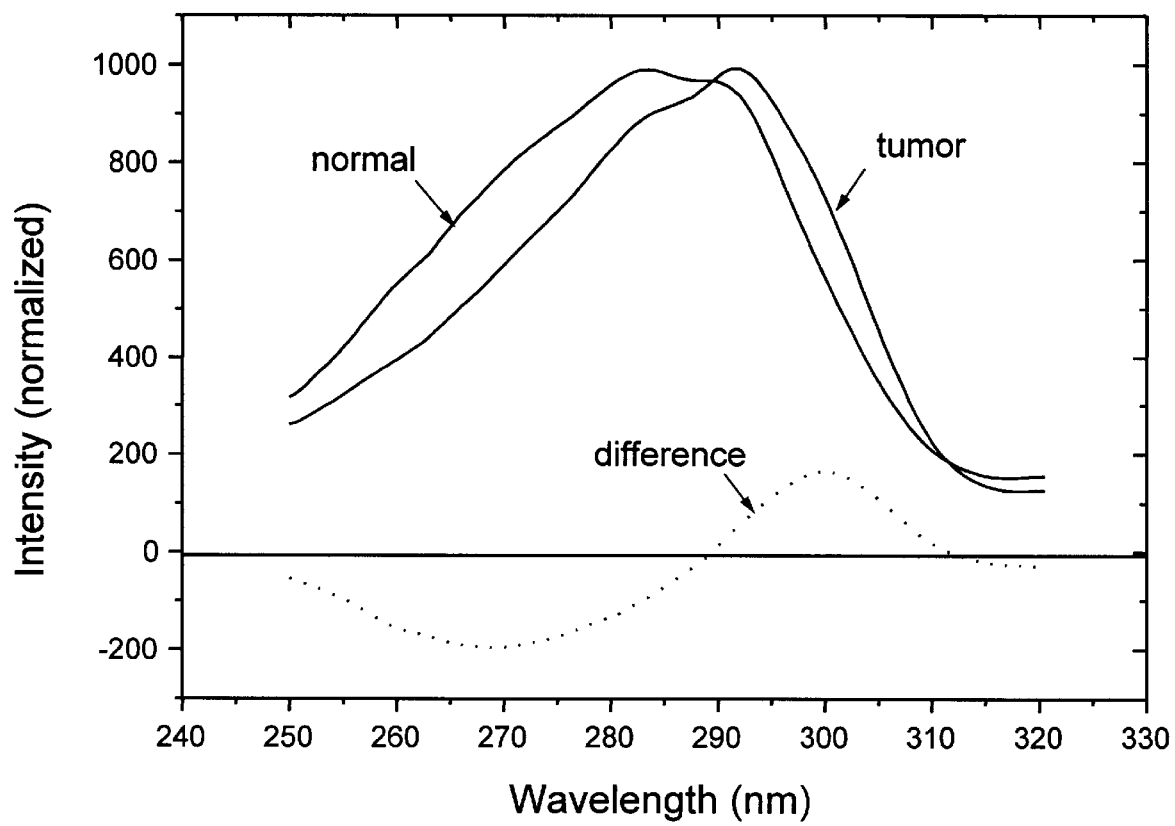
FIG. 4 is a graphic representation of excitation spectra from 250 nm to 320 nm measured at 340 nm emission for normal and cancerous breast smears.

Referring now to FIG. 4, there are shown excitation spectra from 250 nm to 320 nm measured at 340 nm emission for normal and cancerous breast smears. As can be seen, the spectrum for the normal smears has more absorption at lower wavelengths, i.e., below 283 nm, and has less absorption at higher wavelengths, i.e., about 283 nm. This result is reversed in the case of the malignant smears. It can also be seen that the spectrum for the malignant smears is red-shifted relative to that for the normal smears. In order to find a diagnostic value from this data, two ratio values are introduced: $R_{e3} \equiv I_{283}/I_{265}$ and $R_{e4} \equiv I_{283}/I_{293}$ where $I_{265}$ and $I_{293}$ are intensities of the peaks of the difference spectrum and $I_{283}$ is the intensity of the isosbestic point. $R_{e3}$ is 1.82 for malignant smears and 0.979 for normal smears. This two fold increase in the ratio for the malignant smears is due to its less absorption at 265 nm than at 283 nm as compared to the normal smears. $R_{e4}$ is 1.07 for the malignant smears and 1.43 for the normal smears for a similar reason.

Figure 5:
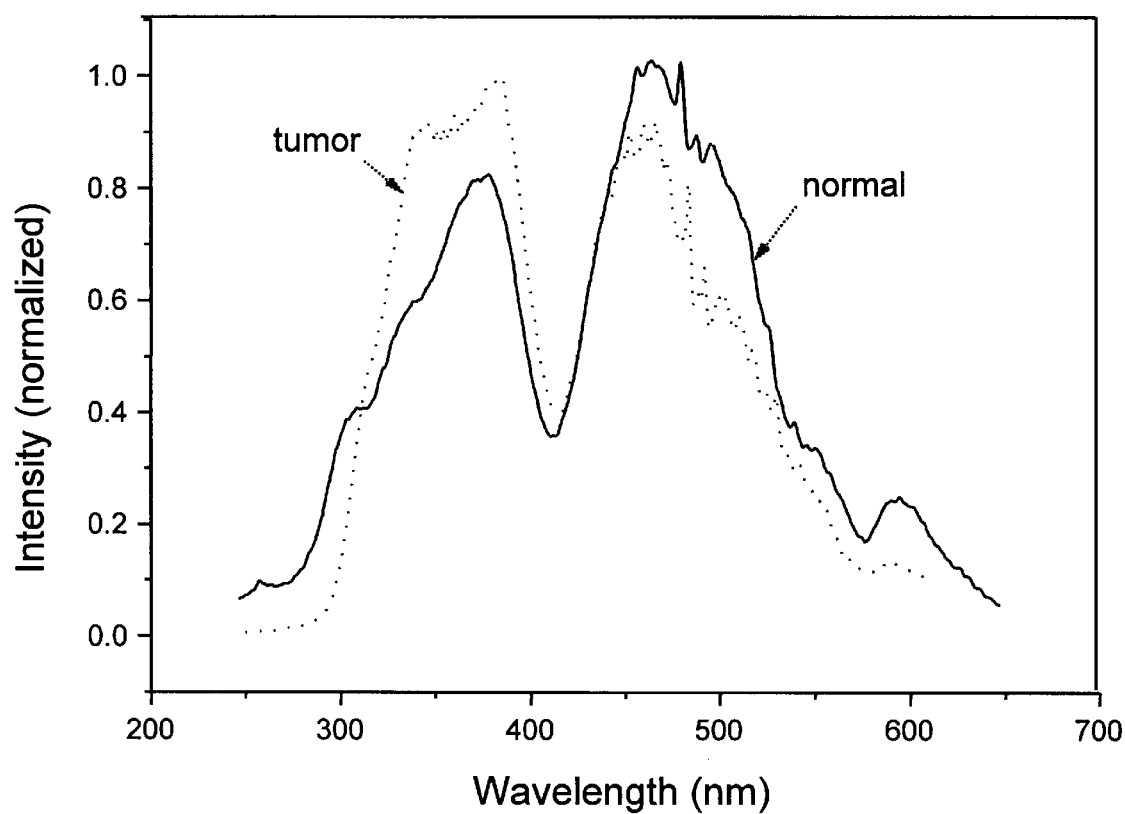
FIG. 5 is a graphic representation of the diffuse reflectance spectra of malignant and normal breast smears.

Referring now to FIG. 5, there is shown the diffuse reflectance spectra of malignant and normal breast smears. As can be seen, there is no considerable difference between the two spectra.

Figure 6A:
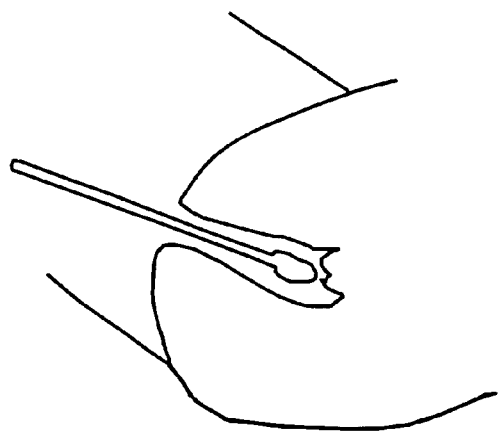
FIGS. 6(a) through 6(c) are schematic views illustrating one type of procedure by which smears for use with the present invention may be made and stored.
Figure 6B:
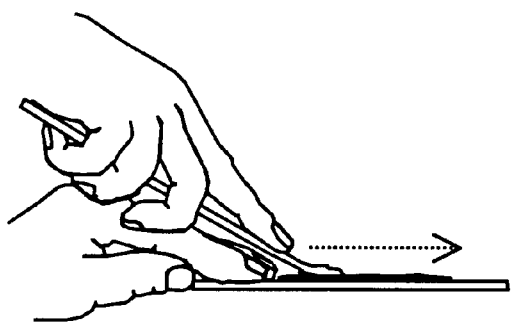
Figure 6C:
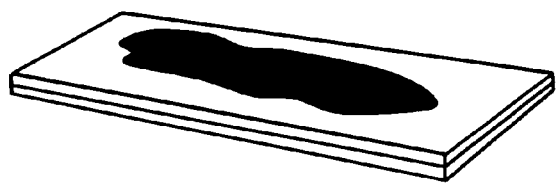
Figure 7A:
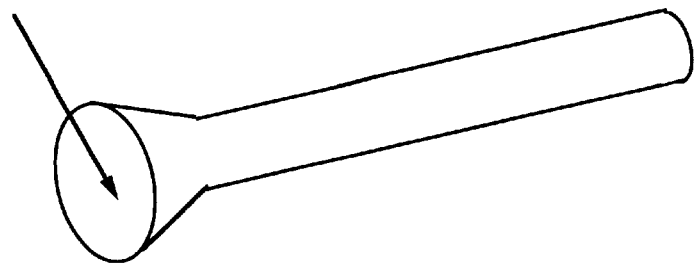
FIGS. 7(a) through 7(c) are schematic views illustrating another type of procedure by which smears for use with the present invention may be made and stored.
Figure 7B:
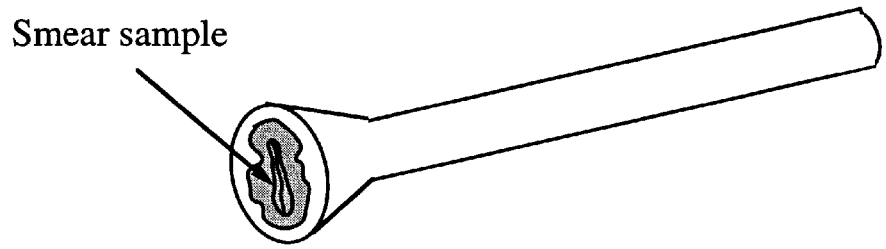
Figure 7C:
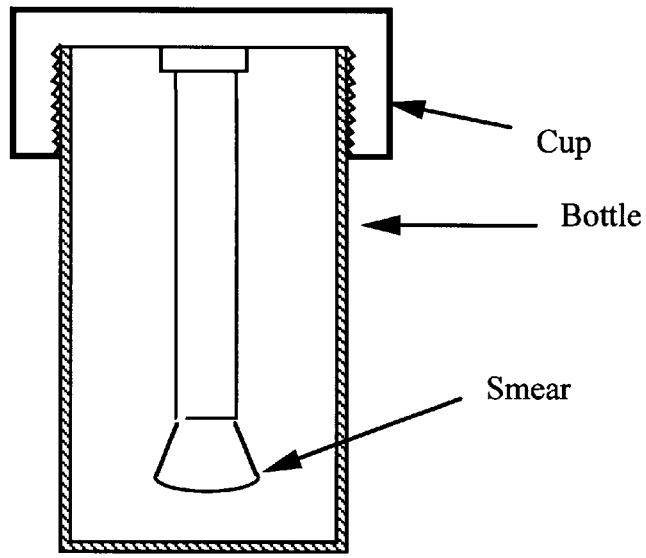

In FIGS. 6(a) through 6(c), there are shown schematic views illustrating one type of procedure by which smears for use with the present invention may be made and stored. In FIGS. 7(a) through 7(c), there are shown schematic views illustrating another type of procedure by which smears for use with the present invention may be made and stored.

Figure 8:
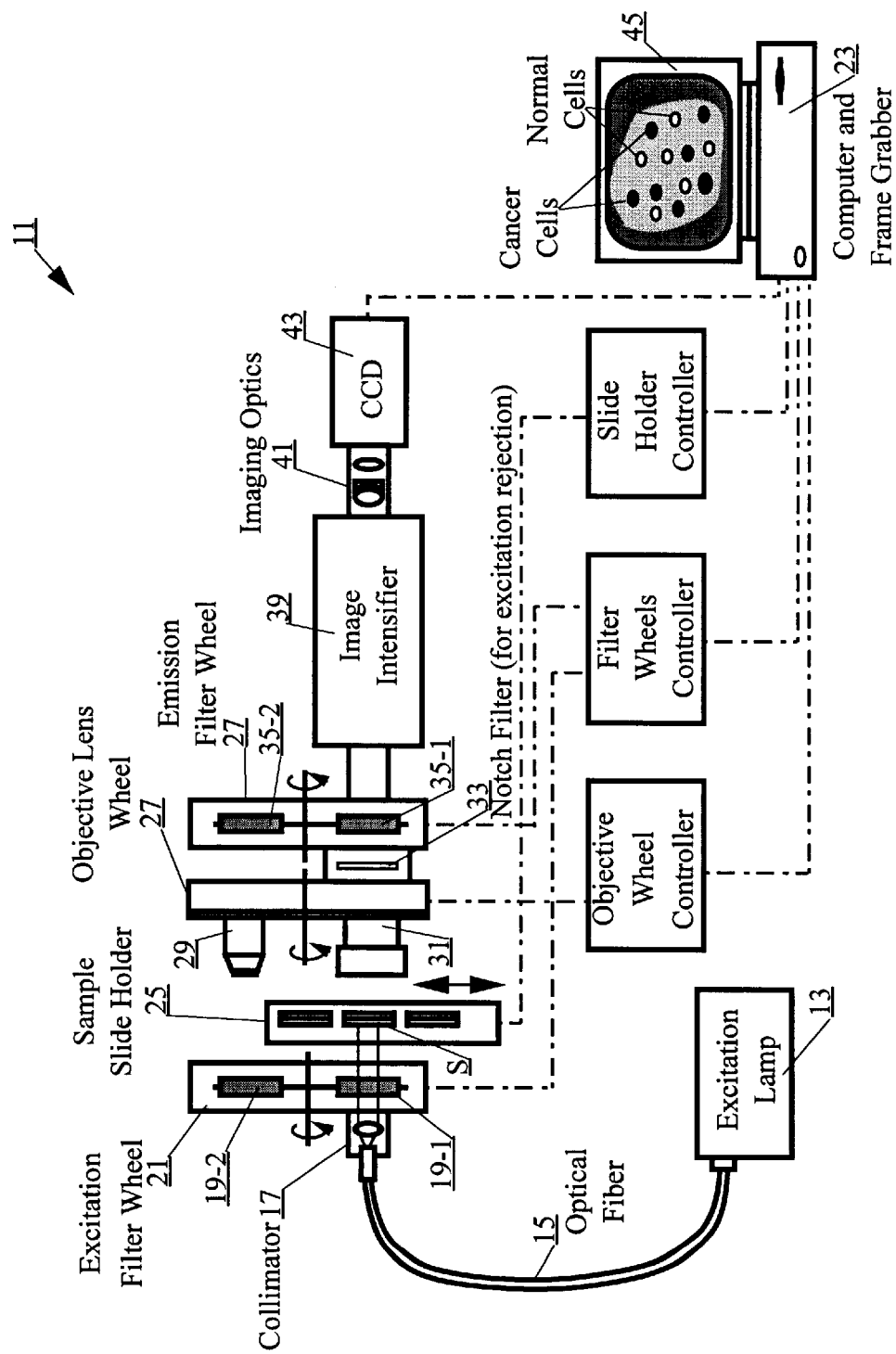
FIG. 8 is a simplified schematic diagram of a first embodiment of an automated system constructed according to the teachings of the present invention for examining a cell smear for the presence of cancerous or precancerous cells therein.

Referring now to FIG. 8, there is shown a simplified schematic view of a first embodiment of an automated system constructed according to the teachings of the present invention for examining a cell smear for the presence of cancerous or precancerous cells therein, the system being represented generally by reference numeral 11.

System 11 comprises an excitation lamp 13 for producing light to excite an area of a smear sample disposed on a quartz slide S. Lamp 13 is preferably a Xenon lamp. The input end of an optical fiber 15 is coupled to the output of lamp 13, fiber 15 being used to transmit the light emitted by lamp 13 to the vicinity of the smear being examined. The light emitted from the output end of fiber 15 is then collimated by a collimator 17. The collimated light is then transmitted through one of a plurality of filters 19-1 and 19-2 mounted in a filter wheel 21, the orientation of filter wheel 21 being controlled by a computer 23. Each of filters 19-1 and 19-2 is selective for a different excitation wavelength (e.g., 260 nm, 280 nm). The filtered light then illuminates a portion of the smear sample on slide S. Slide S is mounted on a multiple slide, movable holder 25, the movement of slide holder 25 being controlled by computer 23.

System 11 also comprises a multiple objective lens wheel 27, wheel 27 holding a plurality of magnifying lenses (at least one of said lenses being a microscopic objective 29 for magnifying the image of the cells of the smear and one of said lens being a standard lens 31). Wheel 27, which is controlled by computer 23, is positioned behind the smear being examined so that the fluorescent light emitted from the smear is collected in a transmission geometry. The magnified light is then passed through a notch filter 33 for filtering out any of the excitation light and then is passed through one of a plurality of emission filters 35-1 and 35-2 mounted in a filter wheel 37, the orientation of filter wheel 37 being controlled by a computer 23. Each of filters 35-1 and 35-2 is selective for a different emission wavelength (e.g., 340 nm, 440 nm). The output of filters 35-1 and 35-2 is then transmitted to an image intensifier 39 and, thereafter, focused by imaging optics 41 onto a CCD camera 43. The output of camera 43 is then transmitted to computer 23, where the measurements are analyzed in the manner described above, and a map of the illuminated area of the smear is displayed on a monitor 45, the map identifying the condition of the cells located therewithin by color or shading for visual inspection. Computer 23 may also be used to generate a count of the number of cancerous or precancerous cells detected.

For emission measurements, filter 19-1 may be selective for light at 280 or 300 nm, with filters 35-1 and 35-2 being selective for light at 340 nm and 440 nm, respectively. For excitation measurements, filters 19-1 and 19-2 may be selective for light at 260 nm and 280 nm, respectively, with filter 35-1 being selective for light at 340 nm.

As can readily be appreciated, one advantage of system 11 is that permits a real-time display of the smear being examined. In addition, system 11 is automated and determinations of the condition of a cell are made based on objective criteria.

Figure 9:
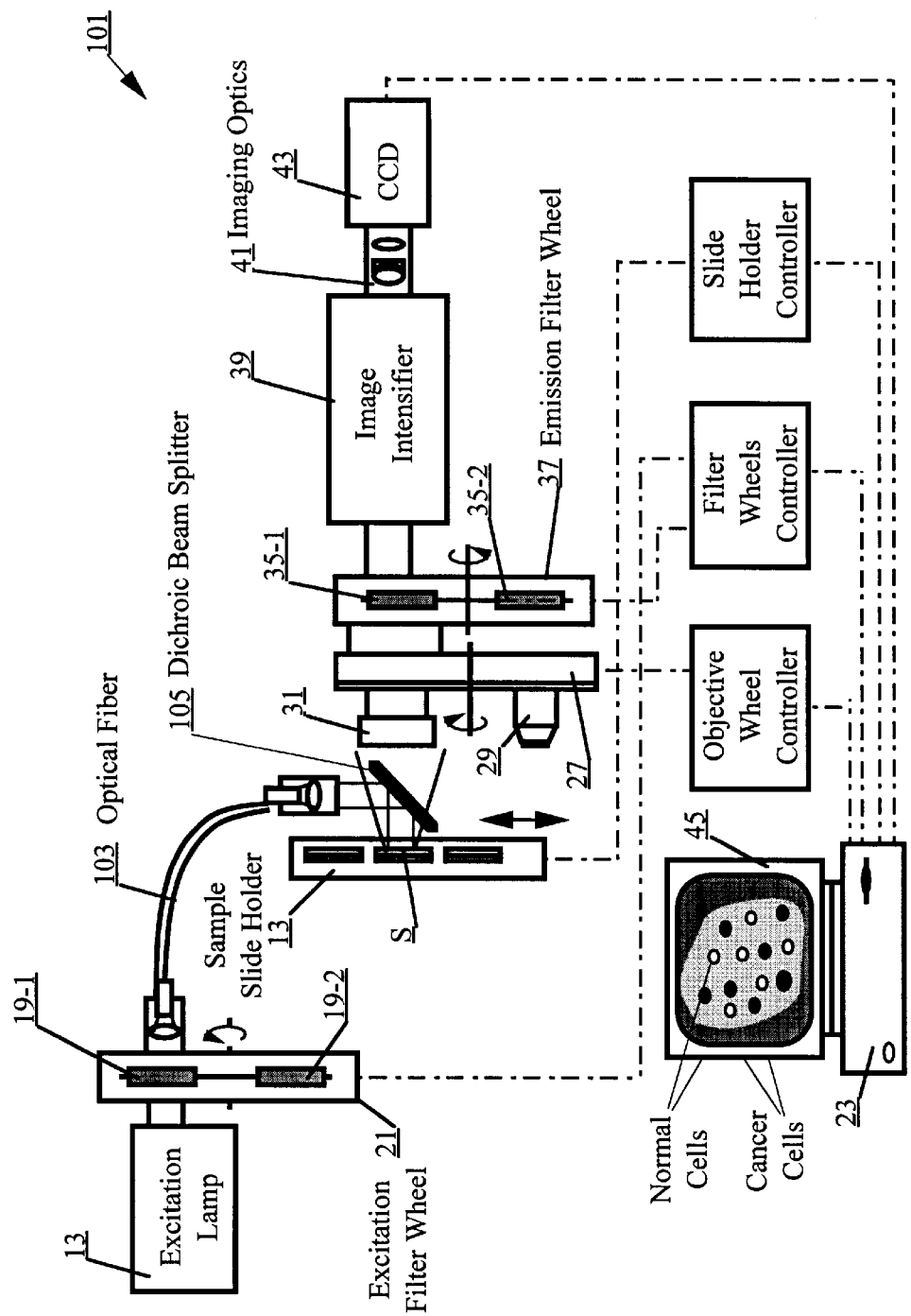
FIG. 9 is a simplified schematic diagram of a second embodiment of an automated system constructed according to the teachings of the present invention for examining a cell smear for the presence of cancerous or precancerous cells therein.

Referring now to FIG. 9, there is shown a simplified schematic diagram of a second embodiment of an automated system constructed according to the teachings of the present invention for examining a cell smear for the presence of cancerous or precancerous cells therein, the system being represented generally by reference numeral 101.

System 101 is similar in many respects to system 11, the primary difference between the two systems being in the relative positions of the illumination and detection mechanisms, system 11 having the illumination and detection mechanisms aligned in a transmission geometry whereas system 101 has the illumination and detection mechanisms aligned in a reflection geometry. More specifically, in system 101, light emitted from lamp 13 is first passed through one of filters 19-1 or 19-2 of excitation filter wheel 21 and is then transmitted by an optical fiber 103 to the vicinity of the slide S holding the smear sample. The light emitted from optical fiber 103 is then reflected off a dichroic beam splitter 105 onto the smear sample. The light emitted from the smear sample is then transmitted back through dichroic beam splitter 105 to objective wheel 27 for magnification.

One advantage of the frontal excitation of system 101 is its good signal-to-noise capability.

Figure 10:
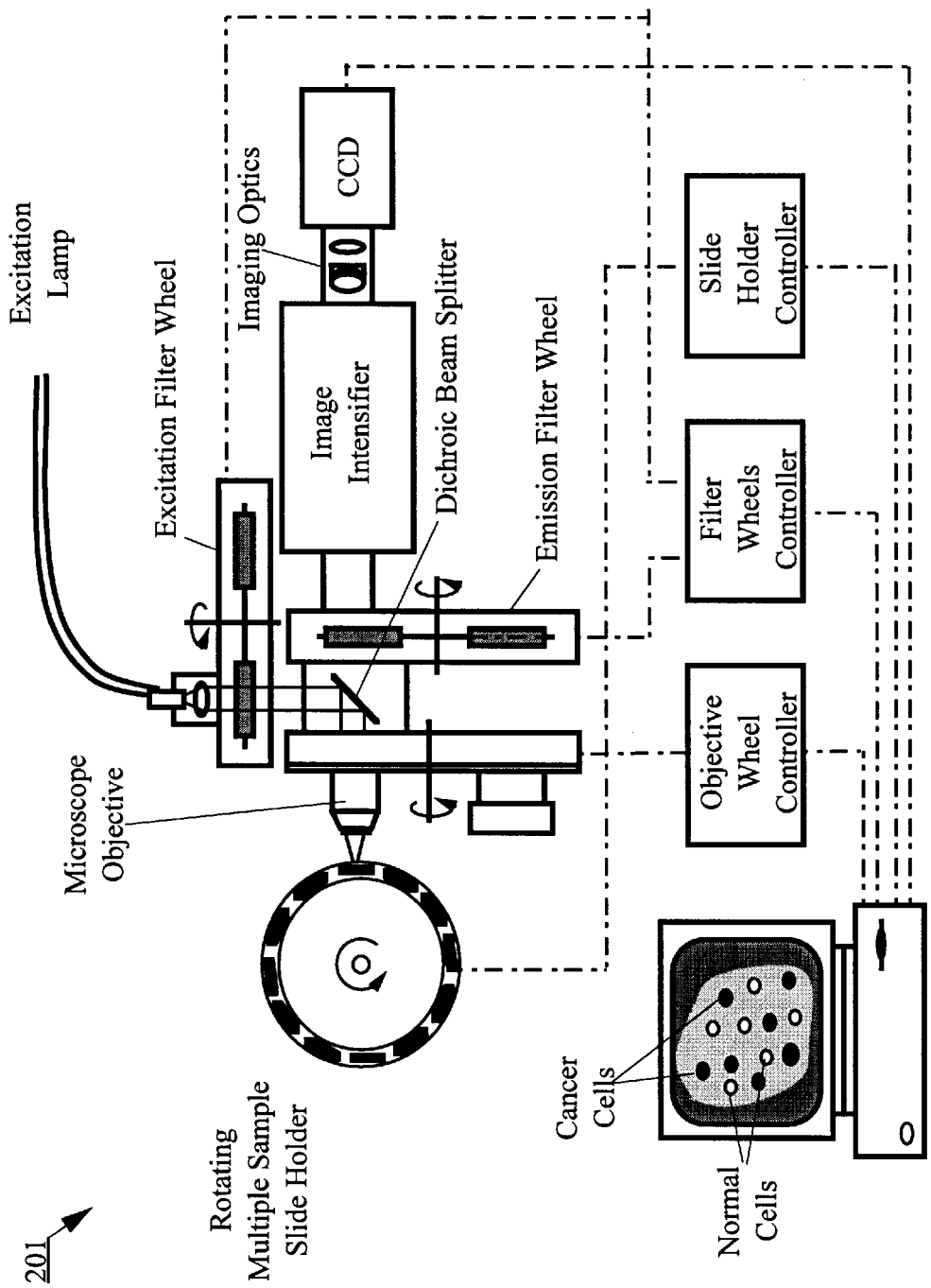
FIG. 10 is a simplified schematic diagram of a third embodiment of an automated system constructed according to the teachings of the present invention for examining a cell smear for the presence of cancerous or precancerous cells therein.

Still another embodiment of an automated system constructed according to the teachings of the present invention for examining a cell smear for the presence of cancerous or precancerous cells therein is shown in FIG. 10, the system being represented generally by reference numeral 201.

The embodiments of the present invention recited herein are intended to be merely exemplary and those skilled in the art will be able to make numerous variations and modifications to it without departing from the spirit of the present invention. All such variations and modifications are intended to be within the scope of the present invention as defined by the claims appended hereto.

What is claimed is:

1. A method of detecting breast cancer or a precancerous breast condition in a patient, said method comprising the steps of:
   (a) obtaining a sample of breast cells from the patient;
   (b) preparing a breast cell smear with said sample of breast cells; and
   (c) using native fluorescence spectroscopy to detect the presence of cancerous or precancerous breast cells in said breast cell smear;
   (d) said native fluorescence spectroscopy using step comprising
      (i) illuminating at least a portion of the breast cell smear with light of a first wavelength, whereby native fluorescence is emitted therefrom,
      (ii) measuring the intensity of native fluorescence emitted from the illuminated area at a second wavelength and at a third wavelength as a function of location within the illuminated area, said first, second and third wavelengths being such that the difference of fluorescence intensities at said second and third wavelengths is indicative of a carcinomatous condition,
      (iii) determining the difference of intensities measured at said second and third wavelengths to obtain a value for each location within the illuminated area; and
      (iv) generating a map of breast cells present within the illuminated area using said values wherein said map indicates the carcinomatous condition of each breast cell therein.

2. A method of detecting breast cancer or a precancerous breast condition in a patient, said method comprising the steps of:
   (a) obtaining a sample of breast cells from the patient;
   (b) preparing a breast cell smear with said sample of breast cells; and
   (c) using native fluorescence spectroscopy to detect the presence of cancerous or precancerous breast cells in said breast cell smear;
   (d) said native fluorescence spectroscopy using step comprising
      (i) illuminating at least a portion of the breast cell smear with light of a first wavelength, whereby native fluorescence is emitted therefrom,
      (ii) measuring the intensity of native fluorescence emitted from the illuminated area at a second wavelength and at a third wavelength as a function of location within the illuminated area, said first, second and third wavelengths being such that the ratio of fluorescence intensities at said second and third wavelengths is indicative of a carcinomatous condition,
      (iii) determining the ratio of intensities measured at said second and third wavelengths to obtain a value for each location within the illuminated area; and
      (iv) generating a map of breast cells present within the illuminated area using said values wherein said map indicates the carcinomatous condition of each breast cell therein.

3. The method as claimed in claim 2 wherein said first, second and third wavelengths are about 280 nm, about 340 nm and about 440 nm, respectively.

4. A method of detecting breast cancer or a precancerous breast condition in a patient, said method comprising the steps of:
   (a) obtaining a sample of breast cells from the patient;
   (b) preparing a breast cell smear with said sample of breast cells; and
   (c) using native fluorescence spectroscopy to detect the presence of cancerous or precancerous breast cells in said breast cell smear;
   (d) said native fluorescence spectroscopy using step comprising
      (i) illuminating at least a portion of the breast cell smear with light of a first wavelength, whereby native fluorescence is emitted therefrom,
      (ii) measuring the intensity of native fluorescence emitted from the illuminated area at a second wavelength as a function of location within the illuminated area,
      (iii) illuminating at least said portion of the breast cell smear with light at a third wavelength, whereby native fluorescence is emitted therefrom,
      (iv) measuring the intensity of native fluorescence emitted from the illuminated area at said second wavelength as a function of location within the illuminated area, said first and third wavelengths being such that the difference of fluorescence intensities at said second wavelength is indicative of a carcinomatous condition, (v) determining the difference of intensities measured at said second wavelength to obtain a value for each location within the illuminated area; and (vi) generating a map of breast cells present within the illuminated area using said values wherein said map indicates the carcinomatous condition of each breast cell therein.

5. A method of detecting breast cancer or a precancerous breast condition in a patient, said method comprising the steps of:

(a) obtaining a sample of breast cells from the patient;

(b) preparing a breast cell smear with said sample of breast cells; and (c) using native fluorescence spectroscopy to detect the presence of cancerous or precancerous breast cells in said breast cell smear;

(d) said native fluorescence spectroscopy using step comprising (i) illuminating at least a portion of the breast cell smear with light of a first wavelength, whereby native fluorescence is emitted therefrom, (ii) measuring the intensity of native fluorescence emitted from the illuminated area at a second wavelength as a function of location within the illuminated area, (iii) illuminating at least said portion of the breast cell smear with light at a third wavelength, whereby native fluorescence is emitted therefrom, (iv) measuring the intensity of native fluorescence emitted from the illuminated area at said second wavelength as a function of location within the illuminated area, said first and third wavelengths being such that the ratio of fluorescence intensities at said second wavelength is indicative of a carcinomatous condition, (v) determining the ratio of intensities measured at said second wavelength to obtain a value for each location within the illuminated area; and (vi) generating a map of breast cells present within the illuminated area using said values wherein said map indicates the carcinomatous condition of each breast cell therein.

6. The method as claimed in claim 5 wherein said first, second and third wavelengths are about 280 nm, about 340 nm and about 260 nm, respectively.

7. The method as claimed in claim 5 wherein said first, second and third wavelengths are about 280 nm, about 340 nm and about 300 nm, respectively.

8. A method of examining a breast cell smear for the presence of cancerous or precancerous breast cells therein, said method comprising the steps of:

(a) illuminating at least a portion of the breast cell smear with light of a first wavelength, whereby native fluorescence is emitted therefrom, (b) measuring the intensity of native fluorescence emitted from the illuminated area at a second wavelength and at a third wavelength as a function of location within the illuminated area, said first, second and third wavelengths being such that the ratio of fluorescence intensities at said second and third wavelengths is indicative of a carcinomatous condition, (c) determining the ratio of intensities measured at said second and third wavelengths to obtain a value for each location within the illuminated area, and (d) generating a map of breast cells present within the illuminated area using said values wherein said map indicates the carcinomatous condition of each breast cell therein.

9. The method as claimed in claim 8 further comprising the step of repeating steps (a) through (d) until the entire cell smear has been examined.

10. A method of examining a breast cell smear for the presence of cancerous or precancerous breast cells therein, said method comprising the steps of:

(a) illuminating at least a portion of the breast cell smear with light of a first wavelength, whereby native fluorescence is emitted therefrom, (b) measuring the intensity of native fluorescence emitted from the illuminated area at a second wavelength as a function of location within the illuminated area, (c) illuminating at least said portion of the breast cell smear with light at a third wavelength, whereby native fluorescence is emitted therefrom, (d) measuring the intensity of native fluorescence emitted from the illuminated area at said second wavelength as a function of location within the illuminated area, said first and third wavelengths being such that the ratio of fluorescence intensities at said second wavelength is indicative of a carcinomatous condition, (e) determining the ratio of intensities measured at said second wavelength to obtain a value for each location within the illuminated area, and (f) generating a map of breast cells present within the illuminated area using said values wherein said map indicates the carcinomatous condition of each breast cell therein.

11. A system for examining a cell smear for the presence of cancerous or precancerous cells therein, said system comprising:

(a) means for illuminating at least a portion of the cell smear with light of a first wavelength, whereby native fluorescence is emitted therefrom, (b) means for measuring the intensity of native fluorescence emitted from the illuminated area at a second wavelength and at a third wavelength as a function of location within the illuminated area, said first, second and third wavelengths being such that the ratio of fluorescence intensities at said second and third wavelengths is indicative of a carcinomatous condition, wherein said measuring means comprises optics for magnifying the light emitted from the cell smear, said optics and said illuminating means being oriented in a transmission geometry, (c) means for determining the ratio of intensities measured at said second and third wavelengths to obtain a value for each location within the illuminated area, and (d) means for generating a map of cells present within the illuminated area using said values wherein said map indicates the carcinomatous condition of each cell therein.

* * * * *